(12) United States Patent
Flynn et al.

(10) Patent No.: US 8,999,650 B2
(45) Date of Patent: *Apr. 7, 2015

(54) MAGNETIC NEEDLE BIOPSY

(75) Inventors: Edward R. Flynn, Albuquerque, NM (US); Richard Larson, Albuquerque, NM (US)

(73) Assignee: Senior Scientific LLC, Albuquerque, NM (US)

( * ) Notice: Subject to any disclaimer, the term of this patent is extended or adjusted under 35 U.S.C. 154(b) by 398 days.

This patent is subject to a terminal disclaimer.

(21) Appl. No.: 13/399,733

(22) Filed: Feb. 17, 2012

(65) Prior Publication Data

US 2012/0149029 A1    Jun. 14, 2012

Related U.S. Application Data

(63) Continuation of application No. 12/337,554, filed on Dec. 17, 2008, now Pat. No. 8,118,754, which is a continuation-in-part of application No. 11/957,988, filed on Dec. 17, 2007, now abandoned, and a continuation-in-part of application No. 11/940,673, filed on Nov. 15, 2007, now Pat. No. 8,060,179.

(60) Provisional application No. 60/549,501, filed on Mar. 1, 2004.

(51) Int. Cl.
| | |
|---|---|
| G01N 33/53 | (2006.01) |
| A61B 10/02 | (2006.01) |
| A61B 19/00 | (2006.01) |
| A61B 17/00 | (2006.01) |

(52) U.S. Cl.
CPC ............. *A61B 10/0233* (2013.01); *A61B 19/54* (2013.01); *A61B 2017/00876* (2013.01); *A61B 2019/5408* (2013.01); *A61B 2019/5454* (2013.01)

(58) Field of Classification Search
CPC ............................................. A61B 2017/00876
See application file for complete search history.

(56) References Cited

U.S. PATENT DOCUMENTS

| | | |
|---|---|---|
| 3,741,198 A | 6/1973 | Burton |
| 4,018,886 A | 4/1977 | Glaever |
| 4,161,943 A | 7/1979 | Nogier |
| 4,346,715 A | 8/1982 | Gammell |
| 4,442,404 A | 4/1984 | Bergmann |
| 4,508,119 A | 4/1985 | Tukamoto |
| 4,574,782 A | 3/1986 | Borrelli |
| 4,590,922 A | 5/1986 | Gordon |
| 4,675,286 A | 6/1987 | Calenoff |
| 4,735,796 A | 4/1988 | Gordon |
| 4,829,984 A | 5/1989 | Gordon |
| 4,950,221 A | 8/1990 | Gordon |
| 5,043,101 A | 8/1991 | Gordon |
| 5,067,952 A | 11/1991 | Gudov |
| 5,203,782 A | 4/1993 | Gudov |
| 5,231,000 A | 7/1993 | Majocha |
| 5,384,109 A | 1/1995 | Klaveness |
| 5,486,161 A | 1/1996 | Lax |
| 5,496,534 A | 3/1996 | Klaveness |
| 5,715,837 A | 2/1998 | Chen |
| 5,735,279 A | 4/1998 | Klaveness |
| 5,738,837 A | 4/1998 | Klaveness |
| 5,759,793 A | 6/1998 | Schwartz |
| 5,782,764 A | 7/1998 | Werne |
| 5,921,244 A | 7/1999 | Chen |
| 5,935,123 A | 8/1999 | Edwards |
| 5,944,023 A * | 8/1999 | Johnson et al. ............... 128/899 |
| 6,203,487 B1 | 3/2001 | Consigny |
| 6,348,185 B1 | 2/2002 | Piwnica-Worms |
| 6,400,980 B1 | 6/2002 | Lemelson |
| 6,459,924 B1 | 10/2002 | Creighton |
| 6,470,220 B1 | 10/2002 | Kraus |
| 6,485,985 B1 | 11/2002 | Weitschies |
| 6,660,002 B1 | 12/2003 | Edwards |
| 6,673,104 B2 * | 1/2004 | Barry ........................... 623/1.15 |
| 6,739,342 B1 | 5/2004 | Fredriksson |
| 6,821,504 B2 | 11/2004 | Wisniewski |
| 6,958,062 B1 | 10/2005 | Gough |
| 6,960,196 B2 | 11/2005 | Prindle |
| 6,997,863 B2 | 2/2006 | Handy |
| 7,053,109 B2 | 5/2006 | Schostarez |
| 7,074,175 B2 | 7/2006 | Handy |
| 7,081,123 B2 | 7/2006 | Merboth |
| 7,459,145 B2 | 12/2008 | Bao |
| 7,662,362 B2 | 2/2010 | Kuppusamy |
| 7,745,001 B2 | 6/2010 | Rosenzweig |

(Continued)

FOREIGN PATENT DOCUMENTS

| | | |
|---|---|---|
| WO | WO01/74374 | 10/2001 |
| WO | WO2005/059118 | 6/2005 |

(Continued)

OTHER PUBLICATIONS

Bryant et al (Phys. Med. Biol. Jun. 8, 2007; 52: 4009-4025).*
Adolphi et al., Characterization of magnetite nanoparticles for Squid-relaxometry and magnetic needle biopsy, Feb. 20, 2009, Journal of Magnetism and Magnetic Materials, vol. 321, Is. 10, p. 1459-1464.
Jaetao et al., Enhanced Leukemia Cell Detection Using a Novel Magnetic Needle and Nanoparticles, Nov. 1, 2009, Cancer Research, Bol. 69, Is. 21, p. 8310-8316.

(Continued)

*Primary Examiner* — Scott Long
(74) *Attorney, Agent, or Firm* — V. Gerald Grafe (57) ABSTRACT

An apparatus and method for performing biopsies in-vivo using magnetically labeled nanoparticles is disclosed. One embodiment of the apparatus is called a magnetic needle. When used in a biopsy, one embodiment of the present invention collects diseased cells in-vivo which have been tagged with magnetic nanoparticles coated with receptors for specific diseased cells.

12 Claims, 8 Drawing Sheets

(56) References Cited

U.S. PATENT DOCUMENTS

| | | | |
|---|---|---|---|
| 7,906,345 B2 | 3/2011 | Wang | |
| 8,118,754 B1 * | 2/2012 | Flynn et al. | 600/562 |
| 2002/0123079 A1 | 9/2002 | Chen | |
| 2002/0177769 A1 | 11/2002 | Orbach | |
| 2003/0028071 A1 | 2/2003 | Handy | |
| 2004/0156784 A1 | 8/2004 | Haase | |
| 2004/0253181 A1 | 12/2004 | Port | |
| 2005/0090732 A1 | 4/2005 | Ivkov | |
| 2005/0249817 A1 | 11/2005 | Haik | |
| 2006/0093555 A1 | 5/2006 | Torres | |
| 2006/0140871 A1 | 6/2006 | Sillerud | |
| 2006/0142749 A1 | 6/2006 | Ivkov | |
| 2007/0037297 A1 | 2/2007 | Yoshinaga | |
| 2007/0112339 A9 | 5/2007 | Ivkov | |
| 2007/0118215 A1 * | 5/2007 | Moaddeb | 623/2.37 |
| 2007/0140974 A1 | 6/2007 | Torres | |
| 2007/0148095 A1 | 6/2007 | Chen | |
| 2007/0166232 A1 | 7/2007 | Cho | |
| 2007/0197900 A1 | 8/2007 | Baudenbacher | |
| 2007/0282200 A1 | 12/2007 | Johnson | |
| 2008/0093219 A1 | 4/2008 | Goldberg | |
| 2009/0074673 A1 | 3/2009 | Janjic | |
| 2009/0156659 A1 | 6/2009 | Butters | |
| 2009/0169478 A1 | 7/2009 | Leuschner | |
| 2009/0243610 A1 | 10/2009 | Ichihara | |
| 2009/0295390 A1 | 12/2009 | Hahn | |
| 2010/0008862 A1 | 1/2010 | Fu | |
| 2010/0021391 A1 | 1/2010 | Douglas | |
| 2010/0047180 A1 | 2/2010 | Zeng | |
| 2010/0120679 A1 | 5/2010 | Xu | |
| 2010/0188075 A1 | 7/2010 | Litvinov | |
| 2010/0219824 A1 | 9/2010 | Sillerud | |
| 2012/0035458 A1 | 2/2012 | Flynn | |
| 2012/0149029 A1 | 6/2012 | Flynn et al. | |

FOREIGN PATENT DOCUMENTS

| | | |
|---|---|---|
| WO | WO2007/021621 | 2/2007 |
| WO | WO2008/133726 | 11/2008 |
| WO | PCT/US2010/051417 | 5/2011 |
| WO | PCT/US2010/055729 | 5/2011 |
| WO | PCT/US2011/28746 | 9/2011 |
| WO | PCT/US2011/036349 | 12/2011 |

OTHER PUBLICATIONS

Stéphane Mornet Sébastien Vasseur, Fabien Grasset and Etienne Duguet, "Magnetic nanoparticle design for medical diagnosis and therapy" Journal of Materials Chemistry, 2004, 14, 2161-2175. retrieved from URL: http://pubs.rsc.org/en/content/articlelanding/2004/jm/b402025a.

Y. R. Chemla H. L. Grossman, Y. Poon, McDermott, R. Stevens, M. D. Alper, and J. Clarke, "Ultrasensitive magnetic biosensor for homogeneous immunoassay" Proc Natl Acad Sci U S A. Dec. 19, 2000; 97(26): 14268-14272, retrieved from URL: http://www.ncbi.nlm.nih.gov/pmc/articles/PMC18907/.

Leslie Laconte Nitin Nitin, Gang Bao, "Magnetic nanoparticle probes", Materials Today, vol. 8, Issue 5, Supplement 1, May 2005, pp. 32-38, ISSN 1369-7021, retrieved from URL: http://www.sciencedirect.com/science/article/B6X1J-4G2FPKYW/2/1301571fec686ec339a119ab10a5e17d.

Nanotechnology tackles brain cancer, National Cancer Institute Alliance for Nanotechnology in Cancer, Dec. 2005, 1-4.

Cecchelli, Romeo et al. Modelling of the blood-brain barrier in drug discovery and development, Nature Publishing Group, vol. 6 Aug. 1007, 650-661.

Cengelli, Feride et al. Interaction of functionalized superparamagnetic iron oxide nanoparticles with brain structures. The Journal of Pharmacology and Experimental Therapeutics vol. 318, No. 1 2006, 108-116.

Flynn, E.R. et al. A biomagnetic system for in vivo cancer imaging. Institute of Physics Publishing, Physics in Medicine and Biology. Phys. Med. Bio. 50 2005, 1273-1293.

Flynn, E.R. et al. Use of a SQUID array to detect T-cells with magnetic nanoparticles in determing transplant rejection. Journal of Magnetism and Magnetic Materials. Www.sciencedirect.com Dec. 2006, 429-435.

Haller, Andreas et al. Low TcSQUID measurement system for magnetic relaxation immunoassays in unshielded environment. IEEE Transactions on Applied Superconductivity, vol. 11, No. 1, Mar. 2001, 1371-1374.

Huddleston, Dan E. et al. Technology Insight: imaging amyloid plaques in the living brain with positron emission tomography and MRI. Nature Publishing Group vol. 1 No. 2. Dec. 2005, 96-105.

Michaelis, K. et al. Covalent linkages of apolipoprotein E to albumin nanoparticles strongly enhances drug transport into the brain. The Journal of Pharmacology and Experimental Therapeutics. vol. 317, No. 3 2006. 1246-1253.

Reddy, G.R. et al. Vascular targeted nanoparticles for imaging and treatment of brain tumors. American Association of Cancer Research. Www.aacrjournals.org. Nov. 15, 2006, 6677-6686.

Small, Gary W. et al. PET of brain amyloid and tau in mild cognitive impairment. The New England Journal of Medicine. Dec. 2006, 2652-2663.

* cited by examiner

MAGNETIC NEEDLE BIOPSY

CROSS-REFERENCE TO RELATED APPLICATIONS

This application is a continuation application of U.S. patent application Ser. No. 12/337,554 filed Dec. 17, 2008, now U.S. Pat. No. 8,118,754, which application was a continuation-in-part application of U.S. patent application Ser. No. 11/957,988, entitled "Magnetic Needle Biopsy", to Edward R. Flynn, Ph.D. and Richard Larson, M.D., Ph.D., filed on Dec. 17, 2007 now abandoned; and which application was a continuation-in-part application of U.S. patent application Ser. No. 11/940,673 filed on Nov. 15, 2007 now U.S. Pat. No. 8,060,179, entitled "Biomagnetic Detection and Treatment of Alzheimer's Disease". This application is related to U.S. patent application Ser. No. 11/069,361, entitled "Magnetic Needle Biopsy", to Edward R. Flynn, Ph.D. and Richard Larson, M.D., Ph.D., filed on Feb. 28, 2005, now U.S. Pat. No. 7,309,316 which claims the benefit of the filing of U.S. Provisional Patent Application No. 60/549,501, entitled "Magnetic Needle Biopsy", filed on Mar. 1, 2004. Each of the preceding is incorporated herein by reference.

BACKGROUND OF THE INVENTION

Field of the Invention (Technical Field)

The present invention relates generally to methods and apparatus for recovering biopsy material, such as bone marrow, bone, and contiguous tissue, from a patient and subsequent collection and storage.

Biopsies are a painful procedure that often have to be repeated a number of times and in several places to achieve sufficient sample for detection of cancer cells. This is particularly true of bone marrow biopsies. In addition, the sensitivity and specificity of the procedure is low in most clinical scenarios.

Bone marrow biopsies consists of puncturing the bone in the iliac crest (pelvis), and obtaining an aspiration of liquid marrow through the hollow needle, followed by a core needle biopsy, which is obtained by breaking off a piece of bone with back and forth, and side to side, movements of the core needle. This procedure is used for diagnostic purposes, for staging patients with various malignancies, and for determining if treated patients have any residual cancer after therapy.

Information from the bone marrow biopsy informs the course of the patient's treatment. Patients with acute leukemia are treated with chemotherapy to put them into remission. There are prognostic variables found prior to treatment that help physicians determine these patients general prognosis and thus tailor their therapy. Thus patients with good prognostic variables may receive less aggressive chemotherapy and still achieve an excellent cure rate.

A bone marrow examination is the generally accepted standard of practice to evaluate malignancy. Morphologic review by light microscopy of bone marrow biopsies has a significant false negative rate between (1-50%) depending on the tumor and tissue type. The false negative rate is the result of two primary factors: 1.) appropriate and adequate sampling of the marrow, and 2.) identification of the tumor cells in the sample. The latter problem has substantially contributed to the false negative rate, but with the advent of polymerase chain reaction, immunoperoxidase staining, and flow Cytometry, the sensitivity of detecting a tumor cell has improved from 1 in 100 to upwards of 1 in $10^3$-$10^6$ cell in many scenarios.

Sampling technology has not changed for over 40 years and the manual bone marrow biopsy has remained essentially unchanged. The ability to adequately sample the bone marrow space is confounded by two major considerations: 1.) The bone marrow space in human adults has several trillion cells, of which approximately 10-50 million are sampled, and 2.) many disease processes do not diffusely infiltrate the marrow space, but occur in multiple foci.

There is growing evidence that an important prognostic indicator is the rate at which patients go into remission. That is, patients achieving a rapid clearance (i.e. negative bone marrow biopsy 14 days after initial chemotherapy) of their leukemia are found to do better than patients who achieve remission over a longer period of time. This has been noted in both acute lymphocytic leukemia, and acute myelocytic leukemia.

However, there are patients who have negative bone marrow biopsies who do poorly, in part due to false negative sampling. Samples from day 14 marrows have very low cellularity due to chemotherapy treatment (less than 1 million cells in many cases). A technology that could increase the sampling of cells without increasing the number of biopsies performed could potentially decrease false negative reports. In addition, proliferation of normal cells (i.e. Hematogones) that morphologically appear as blasts can further confound light microscopy interpretation, and the lack of cells can mitigate adequate evaluation by PCR.

Breast cancer is a common malignancy. There are a number of variables that can be used to assess a patients' prognosis and thus tailor therapy. These include the size and grade of the tumor, and the lymph node status. Recent studies have demonstrated that finding breast cancer cells in a bone marrow biopsy/aspirate performed at the time of the mastectomy has significant prognostic value. Breast cancer commonly invades the marrow in small microscopic foci that may not be sampled with traditional "one pass" bone marrow biopsy. Obtaining biopsy samples through the use of embodiments of the present invention would greatly increase the effective sampling of a biopsy sites such as bone marrow or solid tumor by having the target of interest drawn to the needle rather than having the needle sample the tumor cells. This results in an enriched sample. A biopsy apparatus and method providing for an enriched sample will increase sampling sensitivity and will result in a more effective prognosis and course of action.

Patients with various forms of leukemia, lymphoma and myeloma are treated with autologous hemapoetic stem cell transplants (HSCT). In this procedure, hemapoetic stem cells (HSC) isolated from the patient are reinfused after the patient is subjected to high dose chemotherapy/radiation therapy. Although effective in a number of patients, it has been long recognized that the HSCs can be contaminated with tumor cells. Thus the relapse of the tumor can in some cases be due to this contamination, despite the tumor being eradicated from the patient prior to the reinfusion of the HSC. A number of assays to detect these tumor cells are employed.

The use of magnetic nanoparticles with appropriately-labeled antibodies to target certain specific types of cancer, drug separation and the use of RF heating of magnetic particles for hyperthermia treatment is known (U.S. Pat. Nos. 5,735,279; 5,738,837; 5,043,101; 6,459,924; 5,067,952; 5,203,782; and Proceedings of the Scientific and Clinical Applications of Magnetic Carriers (Hafeli, Urs, Schutt, W., Teller, J., Zborowski, M., (eds.), Plenum Press, NY, 1997; Hafeli, U., Zbrowoski, M., (Eds.) J. Magn. Magn. Mater. 194, 1999; Hafeli, U., Zbrowoski, M., (Eds.), J. Magn. Magn. Mater. 225, 2001). There is a large range of antibodies known for numerous cancer types such as leukemia, breast, prostate, and Hodgkin's disease. There are also known neo-vascular agents, toxins and chemicals that can be attached to magnetic nanoparticles for seeking out tumors, and delivering a compound that will cause harm to the cancer cell.

The magnetic nanoparticles of primary interest are superparamagnetic rather than ferromagnetic providing the important advantages of not attracting each other when not in the presence of an external field and do not form clusters. Superparamagnetic particles exhibit magnetic properties similar to paramagnetic particles in the absence of a magnetic field but have ferromagnetic characteristics such as susceptibilities of many thousands, when in a magnetic field. Exposure to magnetic fields polarize the particles along the field lines and the particles will follow magnetic force lines in a non-uniform magnetic field. Through cell adhesion by antibody action, this force will pull the cell with it. The nano scale interaction between labeled nanoparticles and target can improve the efficiency of biopsies in both bone marrow, solid tumors and serum and reduce the number of biopsies required while increasing the specificity of cancer cell detection.

Magnetic guidance of needle biopsy has previously been disclosed by others. Magnetic guidance results in guiding catheters to the brain and heart to treat blood vessels in the brain and heart. The magnetic guidance method is based on using external electromagnetic coils to move magnetic material wires through blood vessels. The movement is guided by CAT scan imaging and computer control of the force fields exerted by the coils on the wire.

Such advances in the staging of various solid tumors has been led by the advent of CAT scans and more recently PET scans. Patients with a localized tumor often are found to have a small suspicious nodule in a metastatic site and it confirmation is required to determine if these metastatic nodules are malignant for decisions on the correct treatment. It is currently routine clinical practice to biopsy these lesions, often by a CAT scan guided needle biopsy.

Systems and methods previously disclosed have the disadvantage that they do not use magnetic nanoparticles to identify distant tumor/cancer cells by magnetic extraction nor do they have the capability of directly treating these sites with introduction of anti-cancer agents.

BRIEF SUMMARY OF THE INVENTION

One embodiment of the present invention provides for a magnetic biopsy apparatus assembly for obtaining a biopsy sample enriched for diseased cells comprising a cannulae for penetrating a body of a subject having openings at the distal end and proximal end with the cross-sectional area in between the distal end and the proximal end substantially hollow for injecting superparamagnetic nanoparticles into a biopsy site through the cannulae wherein the superparamagnetic nanoparticles are labeled with a receptor for a specific target of interest of a diseased cell and wherein the superparamagnetic nanoparticles do not attract each other in the absence of a magnetic field. The apparatus includes a rod having a distal end and a proximal end with one or more rare-earth magnets located at the distal end of the rod, the rod capable of being inserted into and retracted from the cannulae with the rare-earth magnet portion of the rod positionable partially outside of the distal end of the cannulae and into the biopsy site. The apparatus further includes a sheath that is removably attached to the rod and covers at least a portion of the rod that extends into the biopsy site.

According to another embodiment, a magnetic rod assembly is useful in a method for obtaining from a patient a biopsy sample enriched for diseased cells comprising injecting through the biopsy cannulae into the biopsy site superparamagnetic nanoparticles having a receptor for a specific target of interest of one or more diseased cells. The superparamagnetic nanoparticles injected into the biopsy site within the patient are incubated therein to produce one or more diseased cell-nanoparticle complexes when the target expressed on the one or more diseased cell binds specifically to the receptor on the superparamagnetic nanoparticle. A rod comprising one or more rare-earth magnets at the distal end of the rod is placed through the cannulae and into the biopsy site such that the distal end of the rod extends into the biopsy site wherein the distal end of the rod is covered by a sheath removably attached to the rod. The diseased cell-superparamagnetic nanoparticle complexes are magnetically collecting against the sheath of the rod over a period of time. The rod is removed from the patient through the cannulae with the diseased cell-superparamagnetic nanoparticle complexes magnetically attached to the sheath. The sheath having the diseased cell-superparamagnetic nanoparticle complexes attached thereto is removed from the rod. In an alternative embodiment, the diseased cell-superparamagnetic nanoparticle complexes are examined.

The diseased cell in the biopsy site may be a cancer cell metastasized from breast, prostate, ovary, lung, the liver, or cancer cells in the marrow but is not limited thereto. The biopsy site may be bone marrow, tissue, and serum or any combination thereof. The receptor on the superparamagnetic nanoparticles in one embodiment is an antibody but may be a toxin as an example of a protein or a nucleic acid sequence or combination thereof. The one or more diseased cells from a patient may be in suspension or adherent. In an alternative embodiment, the superparamagnetic nanoparticles are guided to a location of a distant tumor through the use of external magnetic guidance which may be accomplished either manually or automatically.

The one or more diseased cells may be one or more selected from breast cancer cells, prostate cancer cells, ovarian cancer cells, lung cancer cells, liver cancer cells, lymphoma, and melanoma but are not limited thereto as any cancerous cell having a target on its surface is a binding partner for the receptor or ligand on the superparamagnetic nanoparticle is suitable. For example, the receptor is a toxin or drug to destroy the diseased cell in the patient.

In one embodiment of the present invention the incubating step is for a period of time of about 30 seconds to about 10 minutes. In another embodiment of the present invention the magnetically collecting time ranges from about 30 seconds to about 240 seconds. The further analysis or examination of the one or more diseased cell-superparamagnetic nanoparticle complexes is with a microscope.

According to another embodiment of the present invention, a method of obtaining a tissue biopsy sample is described. Paramagnetic or superparamagnetic nanoparticles are injected into a biopsy site through a biopsy cannulae. A rod capable of being magnetized is inserted through the cannulae and is positioned into or near the biopsy site. The rod is magnetized. The superparamagnetic nanoparticles in or near the environment of the biopsy site are collected onto the magnetized rod. The magnetized rod with the paramagnetic or superparamagnetic nanoparticles attached thereto is removed from the cannulae. The paramagnetic or superparamagnetic nanoparticles are collected for analysis.

One embodiment of the present invention preferably comprises a magnetic biopsy apparatus for collecting a biopsy sample of diseased cells from a subject with a sheath. This embodiment preferably comprises a cannulae for penetrating a body of a subject having openings at the distal end and proximal end with the cross-sectional area in between the distal end and the proximal end substantially hollow for injecting superparamagnetic nanoparticles into a biopsy site through the cannulae wherein the superparamagnetic nanoparticles are labeled with a receptor for a specific target of interest of a diseased cell and wherein the superparamagnetic nanoparticles do not attract each other in the absence of a magnetic field. This embodiment further comprises a rod having a distal end and a distal end with a rare earth magnet located at the distal end of the rod, the rod capable of being inserted into and retracted from the cannulae with the rare earth magnet positionable partially outside of the proximal end of the cannulae. The sheath is preferably removably attached to the rod at the distal end and covers the portion of the rod where the rare earth magnet is located.

One aspect of the present invention improves the efficacy of biopsies by reducing the number of biopsies required to determine the presence of cancer and improving the efficiency and specificity.

Another aspect of the present invention improves the identification and isolation of these cells and thus enhance the sensitivity of these tests.

Another aspect of the present invention allows for the biopsy and treatment of distant sites including tumors, cancers, and serum. According to one embodiment of the present invention, this is accomplished through the use of magnetic guidance of the magnetic needle using external magnetic fields controlled by computers.

One aspect of the present invention provides improved efficiency and specificity of biopsies.

Yet another aspect of the present invention improves the sensitivity of biopsies but are less invasive and painful.

BRIEF DESCRIPTION OF THE SEVERAL VIEWS OF THE DRAWINGS

FIG. 2a illustrates a magnetic biopsy device comprising a guidance tube with a central needle containing a stainless steel rod and a magnetic tip on the end of the rod wherein the magnetic tip ranges in size from one (1) cm to five (5) cm in length according to one embodiment of the present invention.

FIG. 2b illustrates a magnetic biopsy device comprising a guidance tube with a ferrous needle attached at one end to a strongly magnetized material according to one embodiment of the present invention.

FIG. 2c illustrates a magnetic biopsy device comprising a guidance tube with a ferrous material attached at one end in addition to a strong electromagnet attached thereto according to one embodiment of the present invention.

DETAILED DESCRIPTION OF THE INVENTION

As used herein "a" means one or more.

According to one embodiment of the present invention, a magnetic biopsy apparatus assembly is similar to a standard biopsy needle with a central shaft and a thin-walled cylindrical channel surrounding the shaft. According to another embodiment of the present invention, a magnetic biopsy device is inserted into the biopsy site, the central piercing shaft is removed and antibody-coated superparamagnetic nanoparticles are injected into the site. Subsequently, a magnitizable rod is inserted into the biopsy channel, a magnetic pole is induced within the rod and magnetically tagged cells are attracted to the rod. The rod with the magnetically tagged cells attached theretoare removed from the site for analysis. The magnetic biopsy apparatus does not require general tissue or marrow samples but specifically collects cells of interest. Bone marrow biopsies are one area of application. Embodiments of the present invention utilize labeled magnetic nanoparticles and a unique "smart" magnetized collection needle.

According to yet another embodiment of the present invention special properties of labeled magnetic nanoparticles and a magnetized needle for collecting these particles after insertion into a biopsy site is described. The biopsy can be of any tissue for example the bone marrow, solid tumors or serum. Magnetic nanoparticles are labeled with molecules for targets of interest.

For example, paramagnetic or superparamagnetic nanoparticles are coated with specific biological coatings to attach to specific biological items including cancer cells, tumor cells, normal body cells, particular proteins, particular antibodies, particular viruses, neovascular structures, and micro vascular structures. For example, the nanoparticles are labeled with antibodies that target CD34 a cell surface marker that is more prevalent on the surface of leukemia cells than on normal leukocytes.

Magnetic fields of one embodiment of the present inventions produces force fields to attract the nanoparticles. Cell adhesion of the antibodies pull the cells with them.

Superparamagnetic nanoparticles have the property that, if no magnetic field is present, (a field smaller or comparable to the earth's field), the particles behave paramagnetic ally, i.e. they have a permeability close to one. However, in a relatively strong magnetic field, they become aligned with that field and exhibit ferromagnetism with permeabilities of several thousand, depending on the particle properties and the strength of the applied magnetic field. This very unusual property means that they can be injected into a volume when there is no applied field without congealing through their own magnetic attraction, but will be strongly attracted to regions of a large applied field. Other bio-materials in the area that are paramagnetic are not affected. Since it is known that millions of antibodies may attach to each cancer cell, a substantial magnetic moment occurs for the each cancer cell producing a significant attractive force in the presence of a large gradient magnetic field source.

Figure 1:
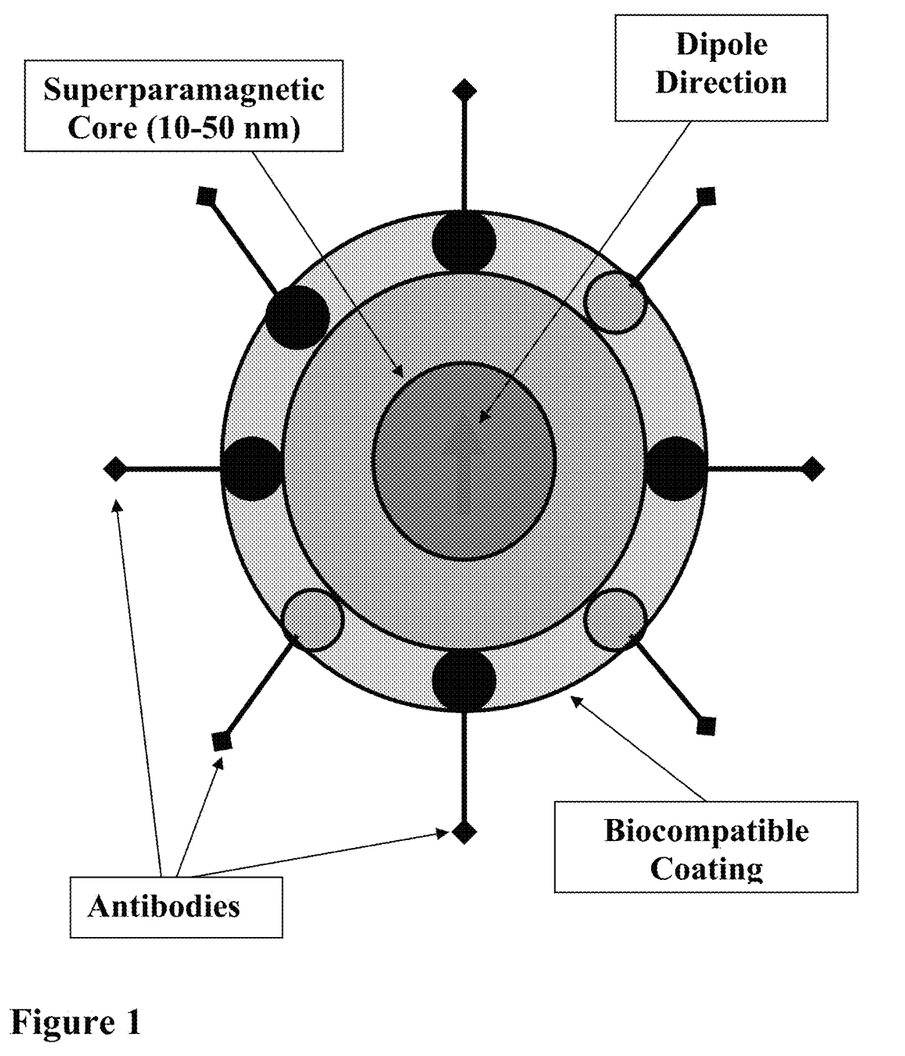
FIG. 1 is a graphical illustration of a magnetic nanoparticle which contains a ferrite core, a coating of a biocompatible material, and a coating of specific antibodies according to one embodiment of the present invention.

Referring now to FIG. 1, the concept of a magnetic nanoparticle coated with an antibody is illustrated according to one embodiment of the present invention. Superparamagnetism considerably enhances the collection of cancer cells in a medium while also increasing cancer specificity through the use of a magnetic biopsy needle. According to one embodiment of the present invention, a magnetic needle biopsy comprises inserting a standard biopsy needle into the bone marrow, and withdrawing the inner rod to permit the injection of antibody-labeled magnetic nanoparticles through the opening of the biopsy needle. After waiting for a specified period, a magnetically tipped rod producing a strong magnetic field is inserted into the tube and left for a pre-determined collection time. The rod (also known as a wire) is removed with the cells containing the magnetic nanoparticles attached thereto. The nanoparticles are collected from the tip of the wire by either a strong magnetic field on the tip, or other mechanisms as described below. The material magnetic nanoparticles are subjected to a magnetic cell sorting process (for example MACS) and the sample is examined for cancer cells. Superparamagnetic properties of the particles also enhance the separation of unbound nanoparticles from those bound to cells.

A typical bone marrow biopsy needle, as currently used in standard biopsies, has a central removable rod with a pointed tip surrounded by an external tube is. The diameter of the central rod is about 1.2 mm. According to one embodiment of the present invention, the central removable rod is replaced by a magnetic rod or needle after initial insertion.

Figure 2:
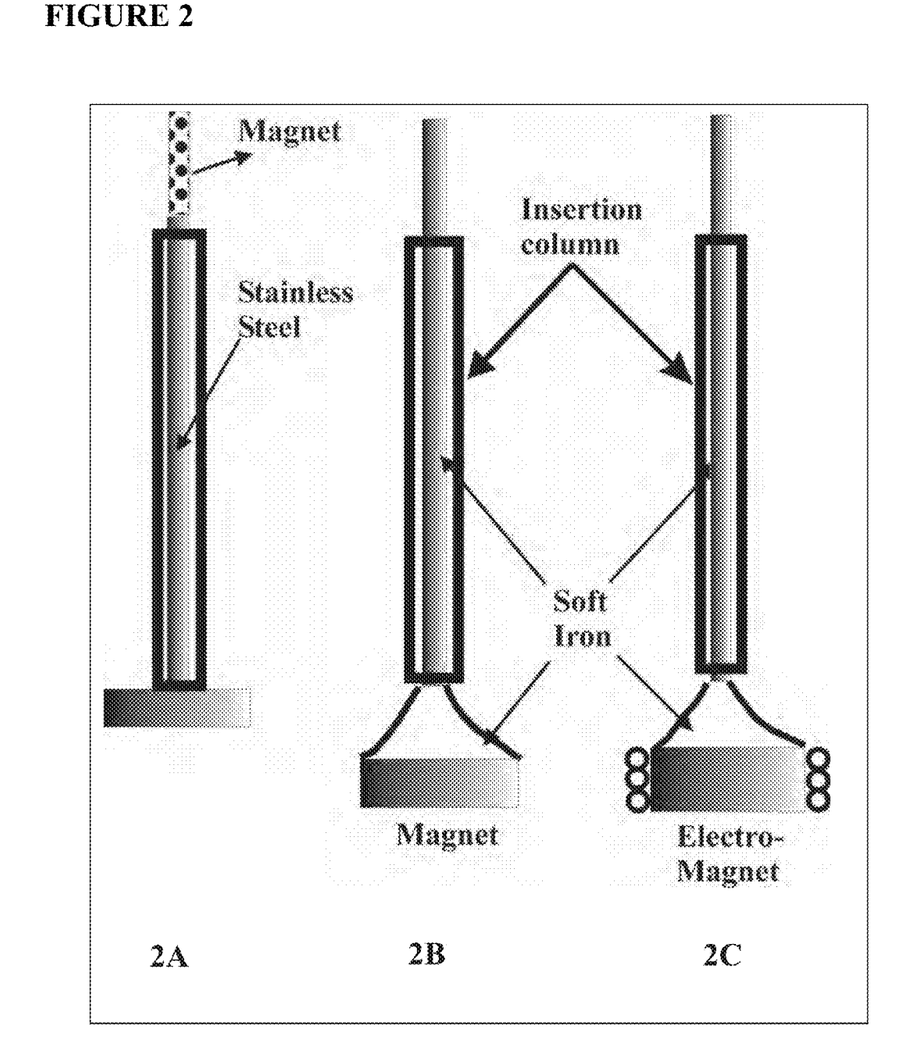
FIG. 2 illustrates three views (FIG. 2a, FIG. 2b, and FIG. 2C) of three magnetic biopsy devices according to different embodiments of the present invention.

Referring now to FIG. 2a, a tip of magnetic material of about 1 cm is located at one end of the central removable rod is illustrated according to another embodiment of the present invention. According to this configuration, magnetic material is located at tissue puncturing end of the rod at about the last cm of the central rod length. Magnetic material such as iron, or rare earth materials such as Knife, Smock, Ceramic, and Alnico are used in these magnetic rods. Magnetic field intensity maximums are about 4000 G for Ceramic 5 and about 13,000 G for Knife-42H with particular values of about 4000 G at the surface of the Knife magnets. The magnetic needle tip is of about one (1) mm diameter and about ten (10) mm length. The magnetic material maybe located at any position along the length of the rod. The dimension of the magnetic needle may range in diameter from about 0.5 mm to about 10 mm. The dimension of the magnetic needle may range in length from about 1 mm to about 1000 mm.

Referring now to FIG. 2b, a magnetic needle with a removable magnet is illustrated according to one embodiment of the present invention. This permits easy removal of the attached nanoparticles from the needle after extraction. In this embodiment, the needle, which is inserted into the biopsy tube, is conically enlarged as it extends beyond the housing of the tube wall or canola and proceeds outside and becomes physically in contact with a larger magnet. This structure permits a concentration of magnetic lines from the magnet located at one end of the rod along the length of the rod to the small tip at the opposing end.

The material and geometry concentrate the greatest flux possible to the tip. A rare earth magnet is attached to the large end so that its magnetic flux lines will proceed through the needle and are emitted at the tip end. In this embodiment of the present invention, large rare earth magnets are used at the end of the rod that is opposite the insertion point, which is not inserted into the patient. The external magnet is removed when the needle is extracted. In the absence of the magnetic field, the nanoparticles are removed from the needle by an additional external magnet extraction.

Referring now to FIG. 2c, an electromagnetic needle is illustrated according o one embodiment of the present invention. In this embodiment an electromagnetic coil wound around a ferromagnetic core and located at the end of the inserted magnetic needle produces the magnetic field. After completion of the biopsy, the external magnet field is turned off when the needle is extracted to remove the nanoparticles from the needle by an additional external magnet extraction.

According to yet another embodiment of the present invention, the biocompatibility of the needle (also known as a wire or rod) that is magnetizable is considered to avoid contact of rare earth magnetic material in the body. The needle material is coated with a thin biocompatible plastic coating to keep it from contacting the tissue. This coating also permits sterilization procedures and potential reuse of the needle.

In another embodiment of the present invention, one means for magnetizing the magnetizable rod is an external magnet. The external magnet is used to increase the magnetic force on the nanoparticles in the vicinity of the needle. The external magnetic pole may be either permanently magnetized or electromagnetic ally excited. The magnetic means can be located on the distal side of the biopsy site away from the biopsy site and used to amplify the collection efficiency of the magnetic rod. This magnetic circuit decreases the nanoparticles collection time at the needle. A rare earth or electromagnetic magnet is placed on the opposite side of the biopsy location to increase the magnetic divergence vector field at the needle location resulting in increase efficiency in collecting magnetic nanoparticles tagged cells. According to one embodiment of the present invention, the external magnet is similar to a commonly used C-magnet where in this case the C surrounds the limb to be biopsied and the needle is attached to one of the C-magnet faces. A Knife magnet, or alternatively an electromagnetic coil giving field strength of 0.6 T generates the magnetic field.

Figure 3:
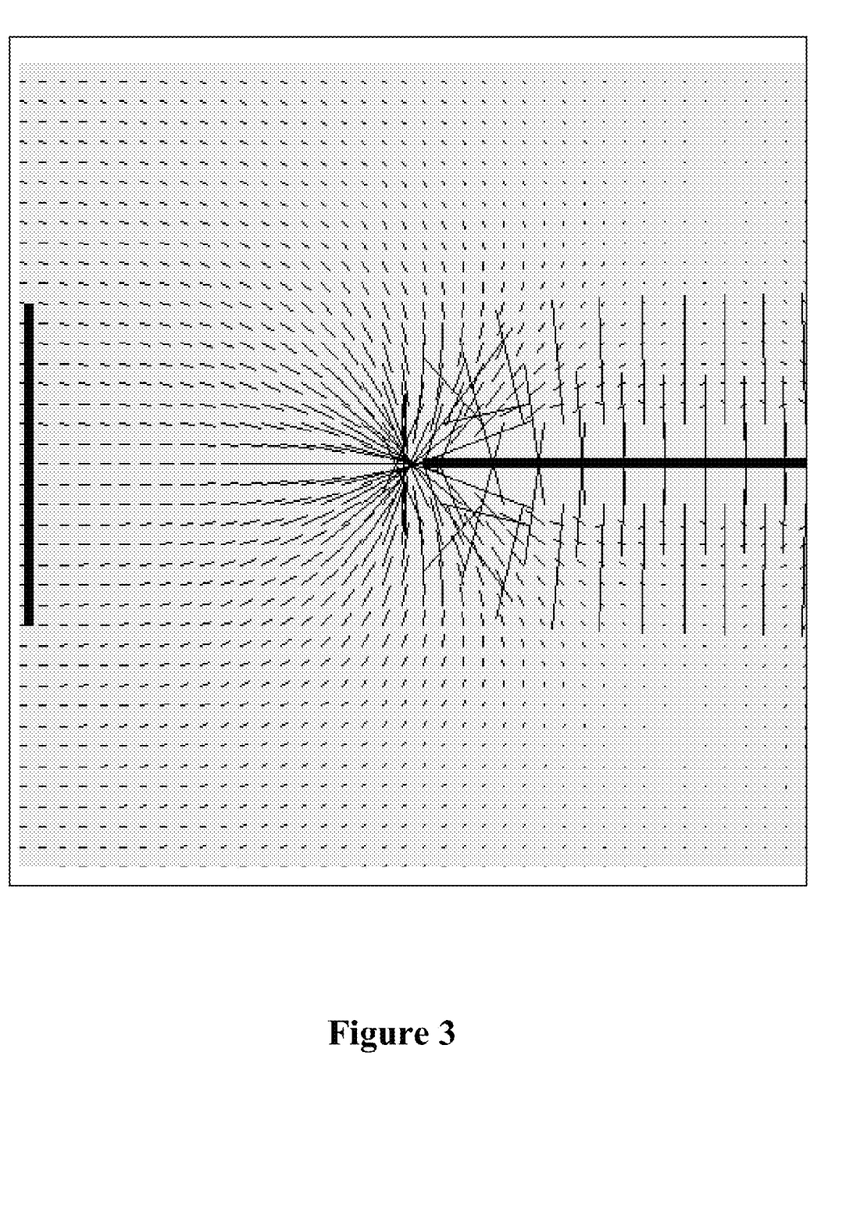
FIG. 3 is a calculation showing the magnetic fields in the vicinity of the magnetic needle.

FIG. 3 illustrates a magnetic field and the field derivatives of the magnetized needle extending to reasonable distances with the magnetizing fields from these magnets according to one embodiment of the present invention. Magnetic field strength from the needle versus distance from needle in a two (2) cm by two (2) cm box.

Figure 4:
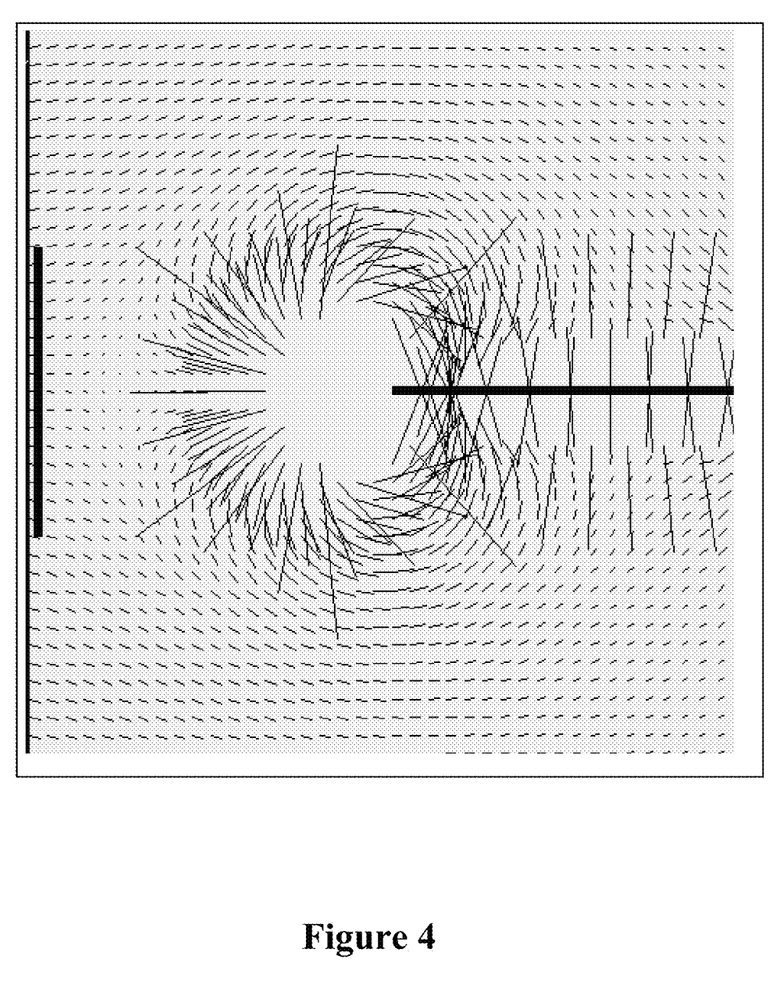
FIG. 4 is a calculation showing the force fields on magnetic nanoparticles in the vicinity of the magnetic needle.

Referring now to FIG. 4, the forces exerted on magnetic nanoparticles can be calculated using electromagnetic theory. Given that the viscosity of the medium is close to water and using Stokes theorem, it is possible to calculate the effective range of attraction and the time to pull the nanoparticles to the needle. Magnetic lines of force on magnetic nanoparticles from the magnetic needle in a two (2) cm by two (2) cm box.

Figure 5:
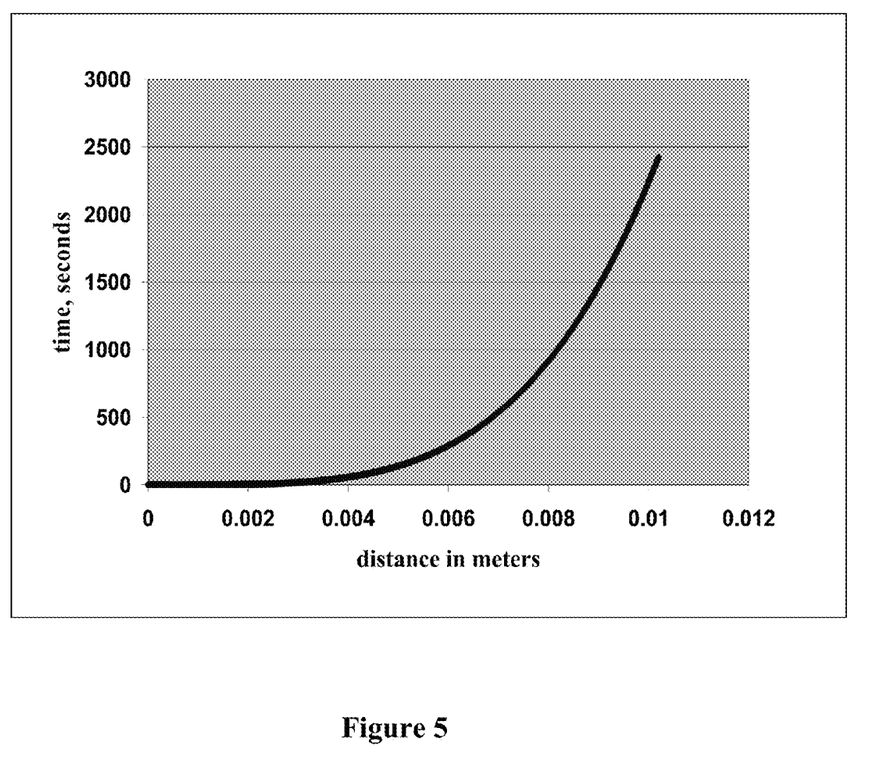
FIG. 5 is a calculation showing the time it takes to pull magnetic nanoparticles onto a magnetic biopsy device as a function of the magnetic nanoparticles initial distance from the needle when the biopsy device is inserted into the biopsy site according to one embodiment of the present invention.

Referring now to FIG. 5, detailed calculations of the forces, ranges, and collection times for various field strengths, needle configurations, and magnetic nanoparticles properties are illustrated in the graph. The time required to pull cells labeled with nanoparticles to the needle to provide the necessary guidance for collection times of the superparamagnetic particles are calculated according to one embodiment of the present invention.

Large number of magnetic nanoparticles attaches to each cell through the antibody mechanism and this adds considerably to the ability to attract the cells to the needle. For example, values of $2\times10^7$ nanoparticles per cell or 30 PG of superparamagnetic iron per cell are achievable. The range of the magnetic needle for attracting magnetic nanoparticles is calculated by modeling the magnetic needle used to collect the cells containing the nanoparticles as a magnetic dipole of dipole moment $\vec{m}$.

In practice, human cancer or other cells are obtained from bone marrow biopsies from clinical examinations of patients suspected of bone marrow disease or metastasis. Magnetically-labeled antibodies directed against CD34 (leukemia cells and myelodysplasia marker) and cytokeratin (breast cancer marker) are one example of nanoparticles utilized. The level of normal cells expressing cytokeratin in normal bone marrow is negligible, and the level of normal cells expressing CD34 is significantly below 1% in normal marrows. Since tumor involves levels upwards of 100% of the marrow, these markers will detect and sample tumor cells preferentially, if the tumor is present. This significantly increases the specificity of the bone marrow biopsy.

In another embodiment of the invention, magnetic guidance methods are used to analyze and treat tumors located at distant sites by guiding labeled paramagnetic or superparamagnetic nanoparticles from the biopsy insertion point to tumors located a sites removed from the biopsy site.

According to another embodiment of the present invention a magnetic biopsy apparatus is located at the end of a long catheter tube containing a wire instead of a magnetic tipped rod. The catheter containing the magnetic wire is guided to the area of interest, e.g. a tumor or cancer, and the central wire withdrawn. Magnetic nanoparticles, labeled with antibodies specific for the type of cancer suspected, are inserted into the tumor and then collected by reinsertion of the magnetic wire as they are in the biopsy method. The application is complex due to the effect of the steering magnets on the entire length of the wire and computer codes are used to control the magnetic steering fields.

A further embodiment of the magnetic biopsy needle approach is the direct injection of therapeutic agents into bone marrow. Upon identification of the type of cancer by the examination of the magnetically extracted cell type, anticancer agents are inserted into the existing biopsy site. Therapeutic drugs could also be injected directly into solid tumors using the magnetic guidance catheter method. Further enhancement would be obtained by attaching magnetic nanoparticles to the therapeutic agents and using the external field coils to further concentrate the particles in the tumor region according to yet another embodiment of the present invention.

In yet another embodiment of the present invention, the biopsy rod or needle has a channel that is formed by a portion of the cross-sectional area from the distal end of the biopsy rod to the proximal end of the biopsy rod being substantially hollow wherein nanoparticles are inserted into the magnetizable biopsy device for delivery to the subject and a biopsy site or a distant tumor location. Additionally, a catheter can be thread through the channel of the biopsy rod and into the subject wherein the catheter delivers nanoparticles to the biopsy site or distant tumor location.

Figure 6:
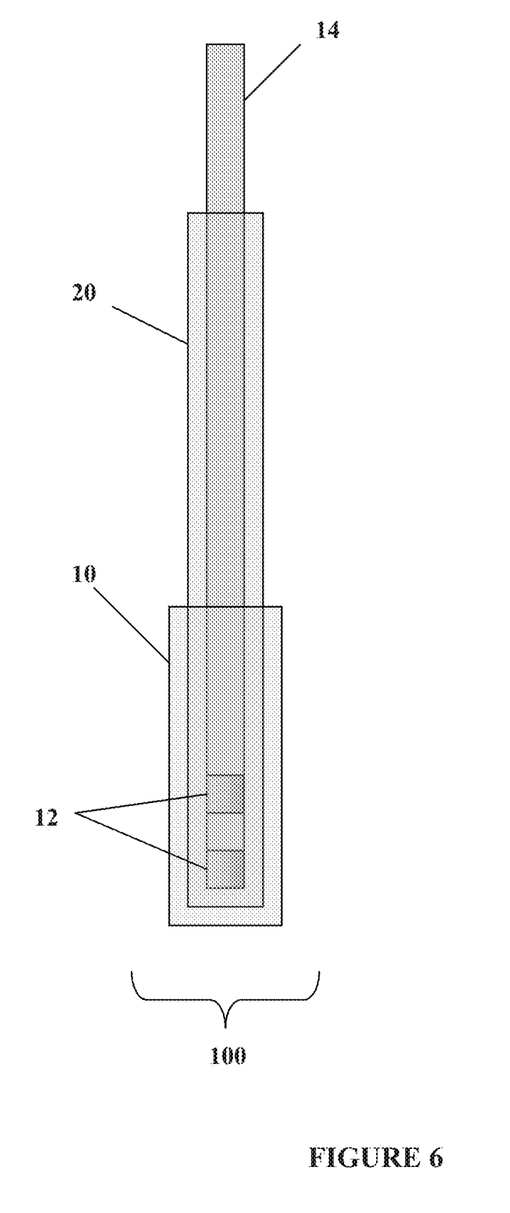
FIG. 6 illustrates an embodiment of the present invention comprising a magnetic biopsy needle insert with a sheath.

Referring now to FIG. 6, one embodiment of the present invention comprises magnetic biopsy apparatus 100 for collecting a biopsy sample of diseased cells from a subject with sheath 10. This embodiment preferably comprises cannulae 20 for penetrating a body of a subject having openings at the distal end and proximal end with the cross-sectional area in between the distal end and the proximal end substantially hollow for injecting superparamagnetic nanoparticles into a biopsy site of a potential through cannulae 20 which contacts the patient at the distal end of the apparatus 100. The superparamagnetic nanoparticles are labeled with a receptor for a specific target of interest of a diseased cell. The superparamagnetic nanoparticles do not attract each other in the absence of a magnetic field.

This embodiment further comprises rod 14 having a distal end and having at least one rare earth magnet 12 located at the distal end of rod 14, rod 14 capable of being inserted into and retracted from cannulae 20 with rare earth magnet 12 positionable partially outside of the proximal end of cannulae 20. Sheath 10 is preferably removable attached to rod 14 at the distal end and covers the portion of rod 14 where rare earth magnet 12 is located. Sheath 10 is preferably polyimide. In one embodiment the sheath 10 is removable attached to the rod 14. The sheath 10 is attached to the rod 14 when the rod 14 is inserted into the biopsy site. The superparamagnetic nano particles are attracted to the rare earth magnets 12 on the rod 14 and are localized on the sheath 10 which is positioned between the rare earth magnet 14 and the superparamagnetic nano particles.

According to one example the rod assembly provides that the length of the rod may be about 18.5 mm and be made of any biocompatible material for example grade 316 stainless steel. The rod may be held in a housing which may run the length of the rod or some portion thereof for example the housing may have a length of about 14 mm and cover the distal tip of the needle where the one or more rare-earth magnets are located. The rare-earth magnets can be of any type for example NdFeB. The housing or a portion thereof may be made from a biocompatible housing for example polyimide. The diameter of the rod assembly can be of any diameter. According to one embodiment the diameter of the rod assembly is about 0.108 mm.

A sheath may cover the housing at the distal end of the assembly where the rare-earth magnets of the rod are located. The sheath may cover only a portion of the rod and have for example a length of about 4.5 mm. The sheath may be removable attached to the housing or to the rod when the housing is not present.

The one or more rare-earth magnets located at the tip of the needle are about 2 mm in length and 1 mm in diameter and separated from each other by about 2 mm according to one embodiment of the present invention. However, the size of the magnets is not limiting and other size magnets would create a similar magnetic force. For example the magnets could range in size from 0.5 to 4 mm. These dimensions and materials are for illustration purposes only and the embodiments of the present invention are not limited to these dimensions or materials.

Acute Lymphoblastic Leukemia (ALL) is the most common leukemia in children. Diagnosis of ALL requires obtaining a sample of bone marrow through bone marrow aspiration, insertion of a needle into a large bone followed by removal of a small amount of liquid bone marrow for examination under a microscope. Once ALL is treated with chemotherapy measurement of minimal residual disease (MRD) continues through repeated bone biopsies. Histological microscope examinations are not sufficient for adequate assessment of MRD or remission status because the threshold of detection is 1-5% of leukemic cells.

Detection of a rare population of cells in the bone marrow would greatly improve the progress and treatment protocells of ALL patients. One embodiment of the present invention enhances sensitivity for measuring small amounts of leukemia cells in the marrow.

EXAMPLE 1

Magnetic nanoparticles conjugated with antibodies for targeting specific eptitopes on an ALL surface, such as a cell surface receptor like CD34 are incubated with a population of cells to be assayed.

A magnetic needle surrounded by a sheath such as plastic according to one embodiment of the present invention is introduced into the cell and magnetic nanoparticle mixture. A plurality of rare-earth magnets at the distal end of the needle attracts magnetic nanoparticle bead complexes as well as nanoparticles uncomplexed to cells. The sheath may extend the length of the magnetic needle or may cover the needle at only a portion of the length. In one embodiment, magnets are about 2 mm in length and are spaced apart from each other at a distance of about 2 mm. Alternatively, a second sheath may surround this assembly for collection of nanoparticles and then removed with the nanoparticles subsequently placed in a solution for microscopic or other type measurements.

Magnetic nanoparticles incubated with target cells and forming a complex are attracted to the magnetic needle when the magnetic needle is put into close proximity to the magnetic nanoparticles. The magnetic nanoparticles through magnetic interaction with the rare-earth magnets locate to the plastic sheath at the distal end of the magnetic needle. Cells bound to the nanoparticle through the antibody are co-located to the needle with the nanoparticle via magnetic forces. The magnetic needle with the magnetic nanoparticles bound thereto are withdrawn from the assay environment. The nanoparticle/cell complexes are removed from the sheath for examination and analysis. For example, the nanoparticles/cell complexes removed from the sheath are analyzed with a SQUID sensor platform wherein the decaying remanence fields from the labeled cells after termination of the magnetic pulse is determined. See Flynn et al, in *Use of a SQUID Array To Detect T-cells With Magnetic Nanoparticles In Determining Transplant Rejection*, Journal of Magnetism and Magnetic Materials, 311, p 429 (2007).

In the present example CD34 Antibodies (Ab) that are specific to common ALL cells were conjugated to magnetic nanoparticles. One or more (for example, thousands of nanoparticles) may be attached to each cell thereby producing a large magnetic moment for attraction to the magnetic needle.

Figure 7:
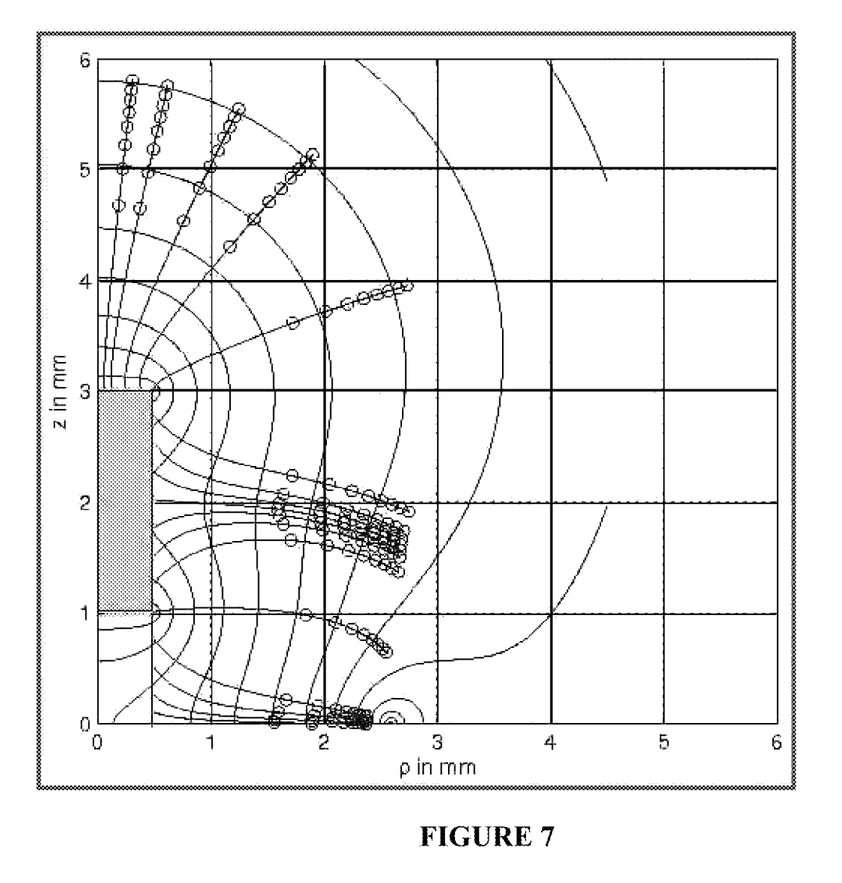
FIG. 7 illustrates magnetic field contour lines for a rare-earth magnet.

Referring now to FIG. 7, a magnetic field contour line graph of the magnetic needle magnet (solid gray bar) and comparison data is illustrated: FIG. 7 contains the magnetic field gradient lines as calculated from the theory. The cells attracted by the magnet will tend to follow these lines. This has been confirmed by movies of particle movement.

Figure 8:
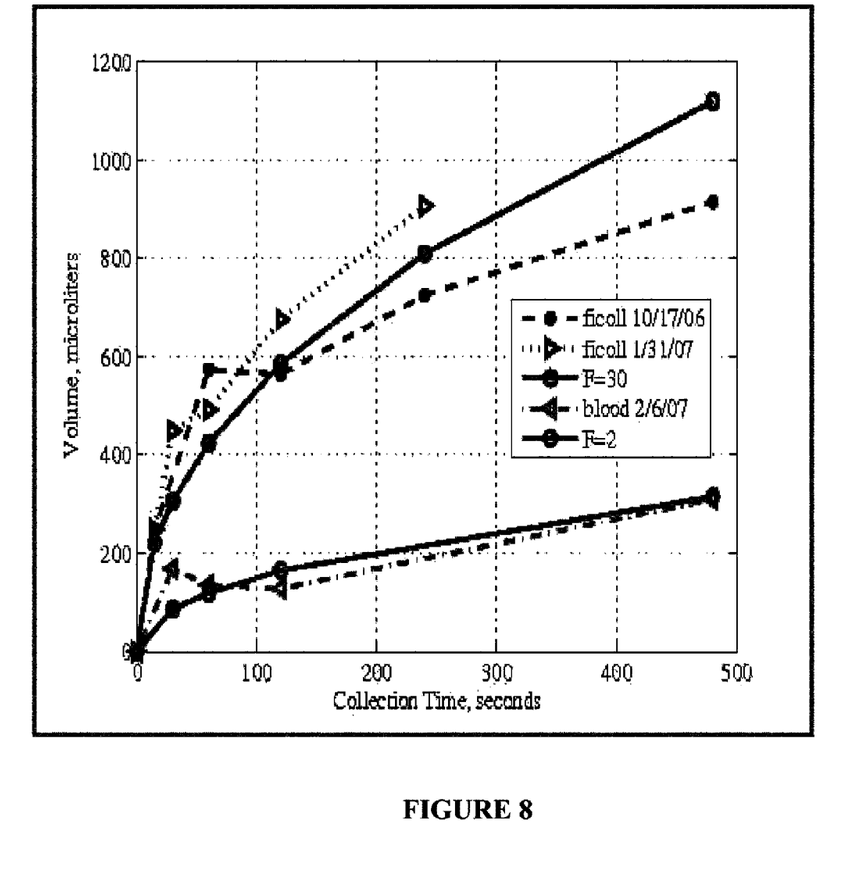
FIG. 8 illustrates calculated collection times for various volumes of cells in suspension.

FIG. 8 illustrates calculated collection times for various volumes using several values of F, where F is for various field strengths of the magnets, from the equations above, representing different viscosities. Experimental data is shown using ficoll and blood to simulate very different viscous media.

Insertion of the magnetic rod in a vial containing recently extracted bone marrow diluted with blood produces a sheath having rings where the cells have been collected due to their complexation with the magnetic nanoparticles. These rings correspond to the regions of highest gradients as shown in the figure above.

In one embodiment of the present invention, the magnetic rod is a magnetic needle. It was unexpectedly observed that a ten fold increase in detection of target cells were observed with the magnetic needle over standard pathology techniques. A standard pathology cell count of 200 cells, noting how many of these were blast cells was conducted for both blood spiked with U937 cells and with fresh bone marrow from leukemia patients. Each case was diluted with blood by factors of two until reduced by 1024 in order to simulate a MRD situation where there will be much fewer blast cells. This was done with the diluted preparation (after nanoparticles were added and incubated), followed by a one minute placement of the magnetic rod in the preparation with a subsequent removal of the collected cells. Table I and Table II give the results from blood spiked with U937 cells and for bone marrow samples from human leukemia cell donors diluted with normal bone marrow.

Table I illustrates the enhancement produced by the rod draws for the number of leukemia cells collected on the rod compared to those directly from the cell preparations results of Table II. A 10 fold increase in the sensitivity for MRD is seen in the rod draws for U937 cells while the number of cells in marrow is magnified by a factor of 5.4 over traditional pathology methods.

TABLE I

| Dilution | U937 Count | Needle Count | Needle Increase |
|---|---|---|---|
| 1/1 | 200/200 | 200/200 | NA |
| 1/2 | 127/200 | 144/200 | 1.13 |
| 1/4 | 71/200 | 94/200 | 1.32 |
| 1/8 | 44/200 | 78/200 | 1.77 |
| 1/16 | 28/200 | 49/200 | 1.75 |
| 1/32 | 13/200 | 32/200 | 2.46 |
| 1/64 | 6/200 | 21/200 | 3.50 |
| 1/128 | 4/200 | 12/200 | 3.00 |
| 1/256 | 2/200 | 7/200 | 3.50 |
| 1/512 | 1/200 | 8/200 | 8.00 |
| 1/1024 | 1/200 | 10/200 | 10.00 |

TABLE II

| Dilution | Marrow Count | Needle Count | Needle Increase |
|---|---|---|---|
| 1/1 | 192/200 | 194/200 | 1.01 |
| 1/2 | 169/200 | 189/200 | 1.12 |
| 1/4 | 148/200 | 151/200 | 1.02 |
| 1/8 | 123/200 | 139/200 | 1.13 |
| 1/16 | 96/200 | 119/200 | 1.24 |
| 1/32 | 79/200 | 103/200 | 1.30 |
| 1/64 | 64/200 | 99/200 | 1.55 |
| 1/128 | 54/200 | 82/200 | 1.52 |
| 1/256 | 39/200 | 79/200 | 2.03 |
| 1/512 | 26/200 | 69/200 | 2.65 |
| 1/1024 | 11/200 | 59/200 | 5.36 |

Although the present invention has been described in terms of various exemplary embodiments for purposes of illustration, those of ordinary skill in the art will appreciate that various modifications and improvement may be made to the described embodiments without departing from the scope of the invention.

What is claimed is:

1. An apparatus for facilitating removal of a substance from an assay environment containing the substance and other constituents, wherein the substance is susceptible to magnetic attraction preferential to at least some of the other constituents, comprising: a housing; a plurality of magnets mounted with the housing such that the magnets are separated from each other, wherein the housing is configured to be inserted into and removed from the assay environment, and wherein the magnetic fields produced by the magnets when the housing is in the assay environment exert sufficient force on the substance that at least some of the substance is removed from the assay environment when the housing is removed from the assay environment; and a sheath removably mounted with the housing such that constituents of the assay environment are prevent by the sheath from physically contacting the housing or the magnets when the apparatus is placed into the assay environment.

2. An apparatus as in claim 1, wherein the magnets comprise rare-earth magnets measuring about 2 mm in a first dimension and about 1mm in a second dimension orthogonal to the first dimension, and wherein the magnets are separated from each other by about 2 mm.

3. An apparatus as in claim 1, wherein the assay environment comprises bone marrow, and wherein the substance is diseased cells to which magnetic nanoparticles have been attached by binding to cell surface features overexpressed in the diseased bone marrow cells relative to other constituents of the bone marrow.

4. An apparatus as in claim 1, wherein the assay environment comprises a bone marrow biopsy.

5. A kit for facilitating removal of a substance from an assay environment, comprising:
- an apparatus as in claim 1;
- a plurality of magnetic nanoparticles conjugated with a targeting agent that binds to the substance preferentially over other constituents of the assay environment.

6. A kit as in claim 5, wherein the magnetic nanoparticles comprise superparamagnetic nanoparticles.

7. A kit as in claim 5, wherein the substance comprises diseased cells, and wherein the targeting agent comprises an antibody that binds with a cell surface feature that is expressed by the diseased cells to a greater extent than expressed by other cells in the assay environment.

8. A kit as in claim 7, wherein the diseased cells comprise leukemia cells, and wherein the targeting agent comprises antibodies directed against CD34.

9. A kit as in claim 5, wherein the assay environment comprises a bone marrow biopsy.

10. A method of determining minimum residual disease present in a leukemia patient, comprising obtaining cells from a bone marrow biopsy, introducing into the cells magnetic nanoparticles that have been conjugated with targeting agents that preferentially bind to cells indicative of minimum residual disease, introducing an apparatus as in claim 1 into the assay environment containing the cells, removing the apparatus from the assay environment, and examining the cells removed from the assay environment by the apparatus to determine minimum residual disease.

11. A method as in claim 10, wherein the targeting agent comprises an antibody directed against CD34.

12. A method as in claim 11, wherein the magnetic nanoparticles comprise superparamagnetic nanoparticles.

* * * * *